United States Patent
Hyde

(12) 
(10) Patent No.: US 6,804,615 B2
(45) Date of Patent: Oct. 12, 2004

(54) METHOD OF ESTIMATING SYSTEM DYNAMICS BY SUBSYSTEM TRANSFER FUNCTION TESTING

(75) Inventor: Tristram T. Hyde, Phoenix, AZ (US)

(73) Assignee: Honeywell International Inc., Morristown, NJ (US)

( * ) Notice: Subject to any disclaimer, the term of this patent is extended or adjusted under 35 U.S.C. 154(b) by 279 days.

(21) Appl. No.: 10/115,722

(22) Filed: Apr. 3, 2002

(65) Prior Publication Data

US 2003/0191600 A1 Oct. 9, 2003

(51) Int. Cl.[7] .......................... G01F 17/00; G01D 3/00; G01H 1/00
(52) U.S. Cl. .............................. 702/56; 72/109; 73/583
(58) Field of Search ............................. 702/33, 41, 42, 702/56, 109; 73/579, 583

(56) References Cited

U.S. PATENT DOCUMENTS

| | | | |
|---|---|---|---|
| 4,061,017 A | * 12/1977 | Sloane et al. | .................. 73/579 |
| 4,761,743 A | 8/1988 | Wittke | |
| 4,777,960 A | 10/1988 | Berger | |
| 5,126,641 A | * 6/1992 | Putman et al. | .............. 318/128 |
| 5,477,453 A | 12/1995 | Harashima | |
| 5,610,843 A | 3/1997 | Chou | |
| 6,341,258 B1 | * 1/2002 | Inoue et al. | ................... 702/56 |

FOREIGN PATENT DOCUMENTS

DE            4238641 A            5/1994

OTHER PUBLICATIONS

Wei Xing Zheng, "Consistent Parameter Estimation of System Transfer Functions Irrespective of Noise Dynamics," Decision and Control, 1997., Proceedings of the 36th IEEE Conference on San Diego, CA, USA Dec. 10–12, 1997, New York, NY. Dec. 10, 1997, pp. 758–763.
(P. 758, col. 1, line 1;—p. 759, col. 2, line 2).

* cited by examiner

Primary Examiner—John Barlow
Assistant Examiner—Meagan S Walling

(57) ABSTRACT

A method according to the present invention calculates a performance function for a structural system (10) that can be used to determine system dynamics at points of interest on the structural system (10). A test input force is applied to an input subsystem (12) and an output subsystem (14) while the motion in response to the test input force is measured to determine a drive point transfer function. A test relative force is applied to the input subsystem (12) and output subsystem (14) at interface points in all degrees of freedom while the motion in response to the test relative force is measured in all degrees of freedom to determine the interface transfer functions. A performance function for the structural system (10) is mathematically calculated based upon the measured drive point transfer functions and interface transfer functions.

23 Claims, 11 Drawing Sheets

$$\overline{Y}_A(i, in) = \frac{\overline{V}_i^A}{\overline{F}_{in}}$$

$$\overline{Y}_A(i, i) = \frac{\overline{V}_i^A}{\overline{F}_i^A}$$

FIG. 5A $$\overline{Y}_i = \frac{\overline{V}_i}{\overline{F}_i} = \frac{\overline{V}_i^B - \overline{V}_i^A}{\overline{F}_i^B - \overline{F}_i^A}$$

FIG. 5B

METHOD OF ESTIMATING SYSTEM DYNAMICS BY SUBSYSTEM TRANSFER FUNCTION TESTING

FIELD OF THE INVENTION

The present invention relates generally to estimating system dynamics, and more particularly to a method of estimating system dynamics by measuring subsystem transfer functions of a system under test.

DESCRIPTION OF THE RELATED ART

The dynamic performance of a structural system composed of a plurality of subsystems, such as a space satellite including a space bus and space payload, can be significantly affected by vibration or shock. The vibration or shock can damage or alter sensitive subsystems of the structural system. The need to understand the effects of vibration and shock on a particular subsystem, as well as on the structural system as a whole, is paramount to obtaining optimal dynamic performance.

Conventional methods perform detailed finite element modeling of all subsystems and the system as a whole in order to determine the effects vibration and shock will have on the system. Initially, a finite element model is generated for each subsystem. The subsystems are subsequently tested using shaker or tap excitation and motion (accelerometer) sensing in a free (suspended) or fixed (bolted to a surface) boundary condition. As the tests are performed, each subsystem finite model is tweaked to better match the test data in a process known as model updating. However, the model updating process provides an estimate of only limited accuracy regarding the effects of vibration and shock on a particular subsystem because the subsystem model never fully converges with the test data.

The tweaked subsystem finite element models are combined into a system model to predict the end-to-end system dynamics. This system model also has only limited system accuracy because it is based upon the individual subsystem models that were never made to fully match the subsystem test data. Regions of the system model that include high interaction between the subsystem models yield even poorer predictions of system dynamics.

After the complete system is built, but before the system is put to use (or launched as in the case of a satellite), a final dynamics test is conducted to verify model fidelity and to check end-to-end performance. Often, the test data is used to further refine the models of the individual parts. However, in the case of large or complex systems, the final dynamics and performance verification test are not feasible due to, for example, schedule or facility constraints.

SUMMARY OF THE INVENTION

In view of the above, the present invention provides a method of predicting system performance by performing subsystem dynamics testing to measure subsystem transfer functions, determining a system performance function based upon the subsystem transfer functions and determining a performance quantity at a specific point of interest from the system performance function. Transfer functions for each subsystem are measured at all degrees of freedom of interest while test forces are applied to each subsystem also at all degrees of freedom of interest. The degrees of freedom of interest include locations and directions where disturbance forces are injected (inputs), where motion affects system performance (outputs) and where the subsystem attaches to other subsystems (interfaces). A system performance function for the structural system as a whole is subsequently determined, and an end-to-end system performance transfer function can be determined based on the measured transfer functions of the subsystems. A system performance quantity can then be accurately estimated from each contributing disturbance.

Through the above method, the present invention provides a method of obtaining an accurate estimate of system performance without having to perform a final dynamics test of the actual system when shock or vibration is applied to individual subsystems within the system.

BRIEF DESCRIPTION OF THE DRAWINGS

Objects and advantages of the present invention will be more readily apparent from the following detailed description of the preferred embodiments thereof when taken together with the accompanying drawings in which:

FIGS. 5A–5D show the derivation of a system performance function when a performance input force is applied to the system in FIG. 1 according to a second embodiment of the methodology of the present invention;

DETAILED DESCRIPTION OF THE PREFERRED EMBODIMENTS

In overview form the present disclosure concerns structural systems designed for space travel. Examples of such systems include space buses that carry space payloads. As further discussed below various inventive principles and combinations thereof are advantageously employed to determine a dynamic performance of the structural system and more specifically to determine the effect dynamic forces applied to the space bus will have on the space payload provided these principles or equivalents are utilized.

The instant disclosure is provided to further explain in an enabling fashion the best modes of performing the embodiments of the present invention. The disclosure is further offered to enhance an understanding and appreciation for the inventive principles and advantages thereof, rather than to limit in any manner the invention. The invention is defined solely by the appended claims including any amendments made during the pendency of this application and all equivalents of those claims as issued.

It is further understood that the use of relational terms such as first and second, top and bottom, and the like, if any, are used solely to distinguish one from another entity, item, or action without necessarily requiring or implying any actual such relationship or order between such entities, items or actions. Much of the inventive functionality and many of the inventive principles are best implemented with or in software programs or instructions. It is expected that one of ordinary skill, notwithstanding possibly significant effort and many design choices motivated by, for example, available time, current technology, and economic considerations, when guided by the concepts and principles disclosed herein will be readily capable of generating such software instructions and programs with minimal experimentation. Therefore, further discussion of such software, if any, will be limited in the interest of brevity and minimization of any risk of obscuring the principles and concepts in accordance with the present invention.

Figure 1:
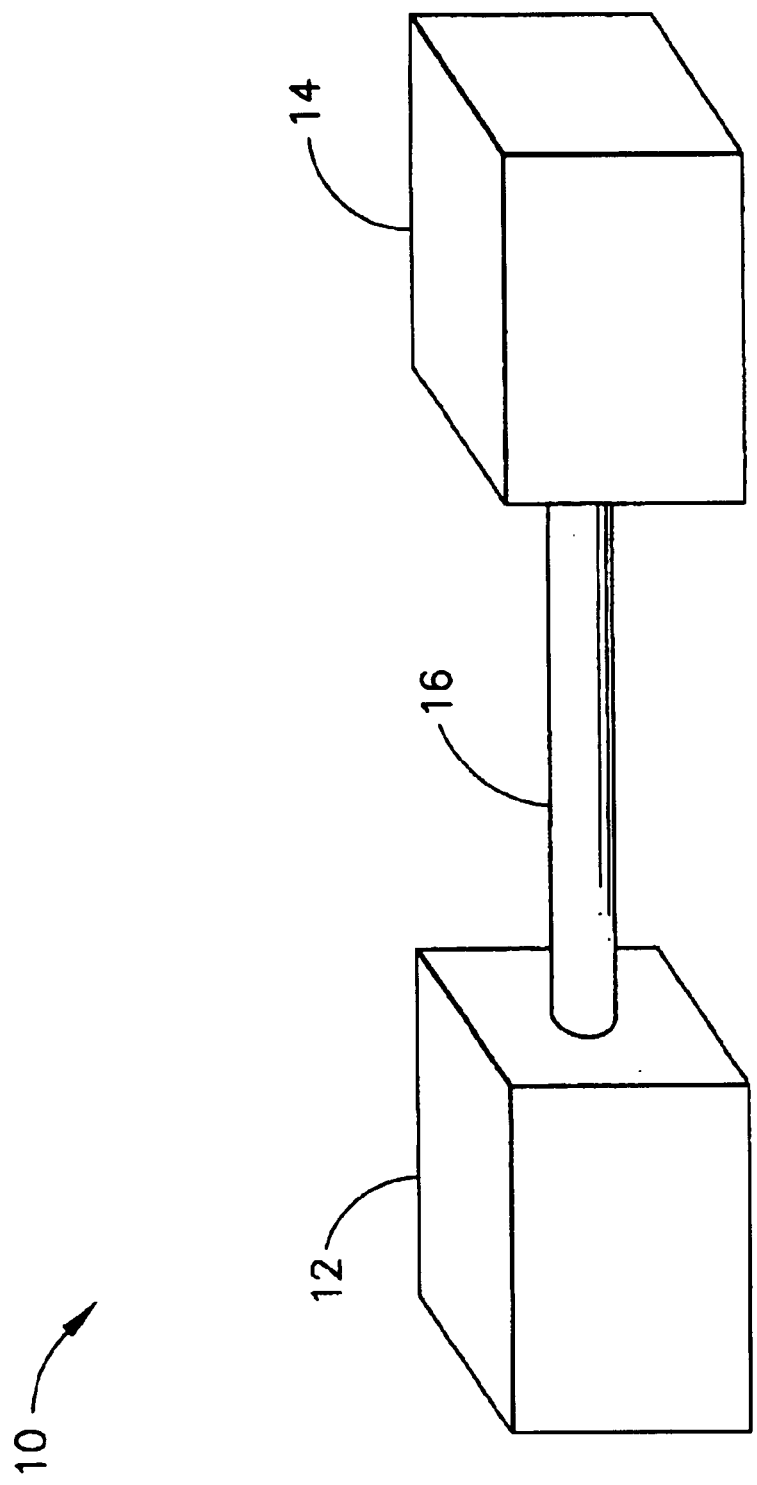
FIG. 1 shows a first exemplary system to be tested by a first embodiment of the methodology of the present invention.

The present disclosure will discuss various embodiments in accordance with the invention. The system diagrams of FIGS. 1–10 will be used to lay the groundwork for a deeper understanding of the present invention and advantages thereof. FIG. 1 in large part and at the simplified level depicted is a representative diagram of a structural system (system) 10 and will serve to explain the problems and certain inventive solutions thereto according to the present invention.

Referring now to the drawings in which like numerals reference like items, FIG. 1 shows a first exemplary system 10 to be tested by a first embodiment of the methodology of the present invention. Specifically, the system 10 includes an input subsystem 12, an output subsystem 14 and an isolator 16. However, in accordance with the methodology of the present invention, the system 10 does not have to be limited to one of each subsystem. Rather, the methodology of the present invention can be implemented in a system with numerous subsystems as long as all of the subsystems are in structural communication with at least one other subsystem. The exemplary system 10 could represent, for example, a structure designed for space travel in which the input subsystem 12 is a space bus and the output subsystem 14 is a payload.

Figure 2A:
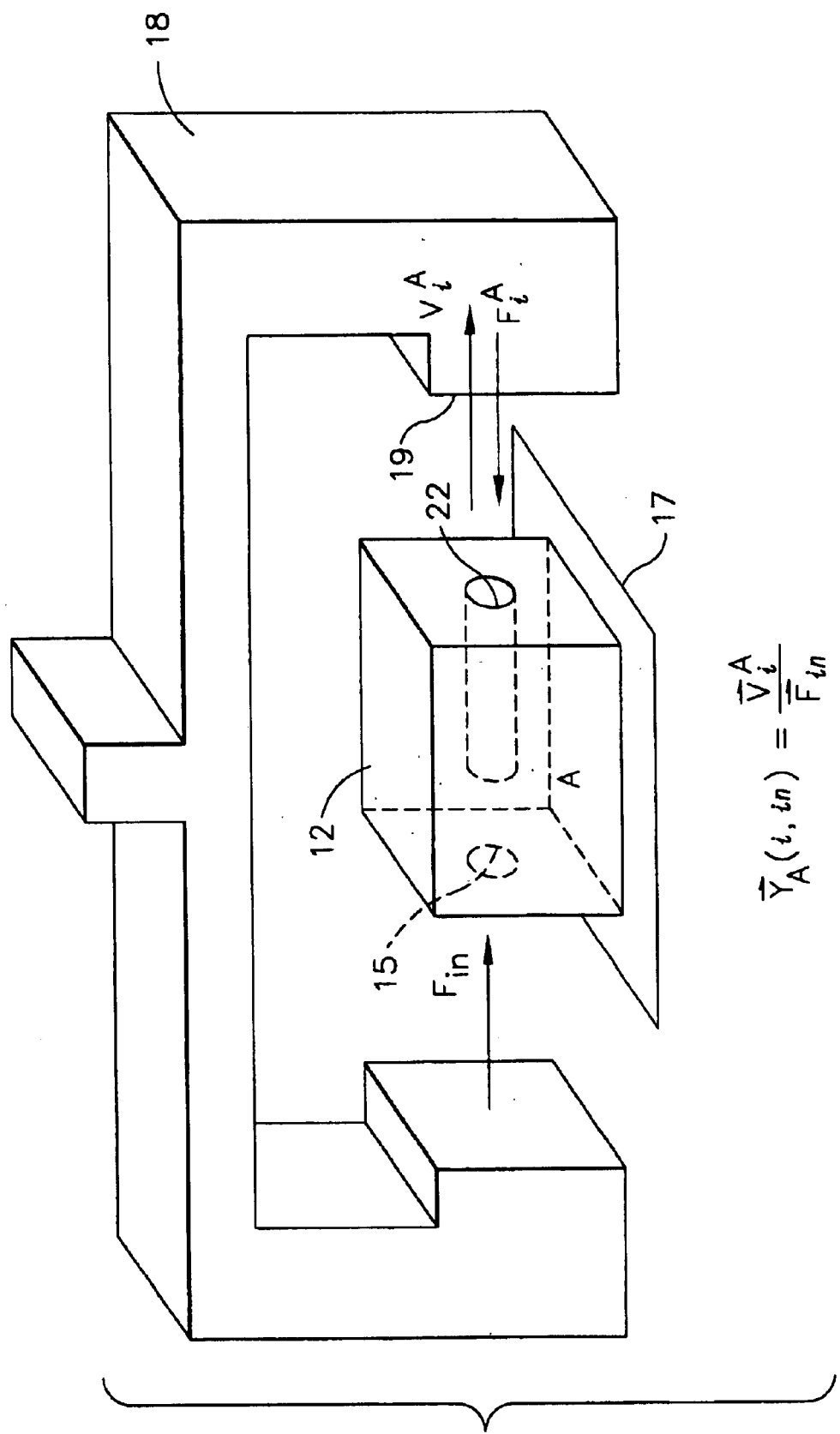
FIGS. 2A–2B show measured subsystem transfer functions for each subsystem of the exemplary system in FIG. 1 when test forces are applied according to the first embodiment of the methodology of the present invention.

Referring generally to FIGS. 2A–4, the first embodiment of the methodology of the present invention will now be more specifically discussed. Referring specifically to FIGS. 2A–2B, the output subsystem 14 and the isolator 16 are considered one subsystem. A test input force $F_{in}$ is applied to a drive point 15 of the input subsystem 12 and a test relative force $F_i^B$ is applied to an interface point 24 of the output subsystem 14. The drive point 15 is a disturbance entry point on a subsystem. For example, a drive point could be a point where a subsystem was connected to a piece of rotating equipment with unbalance. Generally, the interface points 22, 24 are points in which the subsystems interface. More specifically, in the exemplary system 10, the interface point 22 of the input subsystem 12 is a point at which the input subsystem 12 receives the isolator 16 of the output subsystem 14 via coupling. The interface point 24 of the output subsystem 14 is a point in which the isolator 16 of the output subsystem 14 interfaces with the interface point 22 of the input subsystem 12. A sensor 19 measures the responding motion of the input subsystem 12 at the drive point 15 while the test input force $F_{in}$ is being applied and the responding motion of the output subsystem 14 at a performance sensitive point 25 while the test relative force $F_i^B$ is being applied. The test input force $F_{in}$ and the test relative force $F_i^B$ could be applied by, for example, attaching a shaker (not shown) through a force sensor 19 to vibrate the input subsystem 12, or an instrumental hammer (not shown) to tap at the drive point 15 of the input subsystem 12. The sensor 19 could be a motion sensor, such as an accelerometer, and could be combined with the device used to apply the test input force, or the sensor could be a separate device.

Figure 2B:
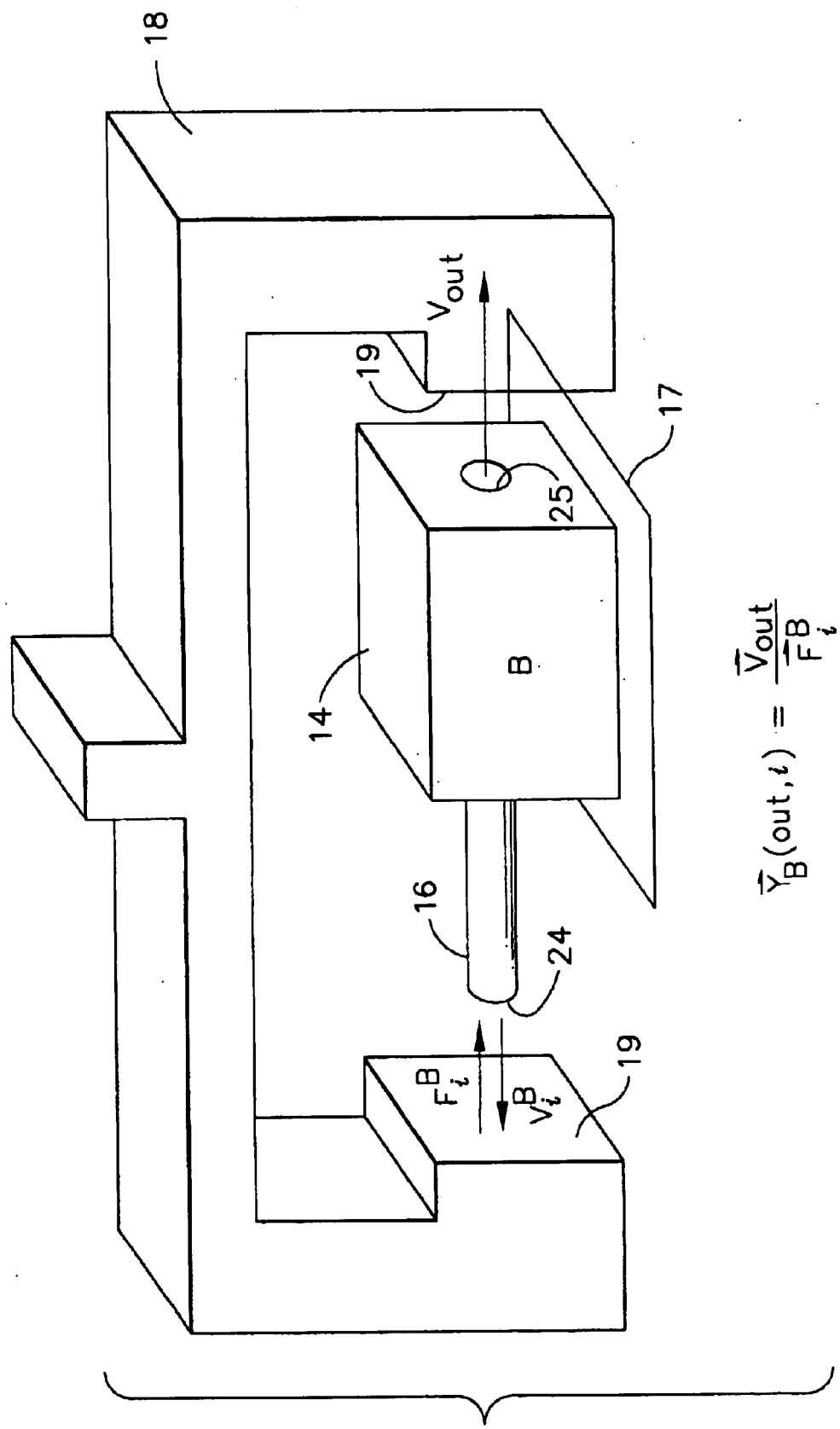

In FIGS. 2A–2B, the input subsystem 12 and output subsystem 14 are shown suspended from a surface 17 while a vibration driver 18 applies various test vibration forces $F_{in}$, $F_i^B$ from one side of the vibration driver 18 and a motion sensor 19 on the other side of the vibration driver 18 senses motion $V_i^A$ by the input subsystem 12 while vibrated. The vibration driver 18 is used to excite vibration (test input force $F_{in}$) through a force sensor at the drive point 15 of the input subsystem 12, while the motion sensor 19 senses the motion at the interface point 22 and is also used to excite vibration (test relative force $F_i^B$) through a force sensor 19 at the interface point 24 of the output subsystem 14 while the motion sensor 19 senses the motion $V_{out}$ at a performance sensitive point 25. The transfer functions are related to the test forces and the motion in response to the test forces by the following formulas:

$$Y_A(i,in)=V_i^A/F_{in} \text{(for the input subsystem 12);} \quad (1)$$

and $$Y_B(out,i)=V_{out}/F_i^B \text{(for the output subsystem 14).} \quad (2)$$

Figure 3A:
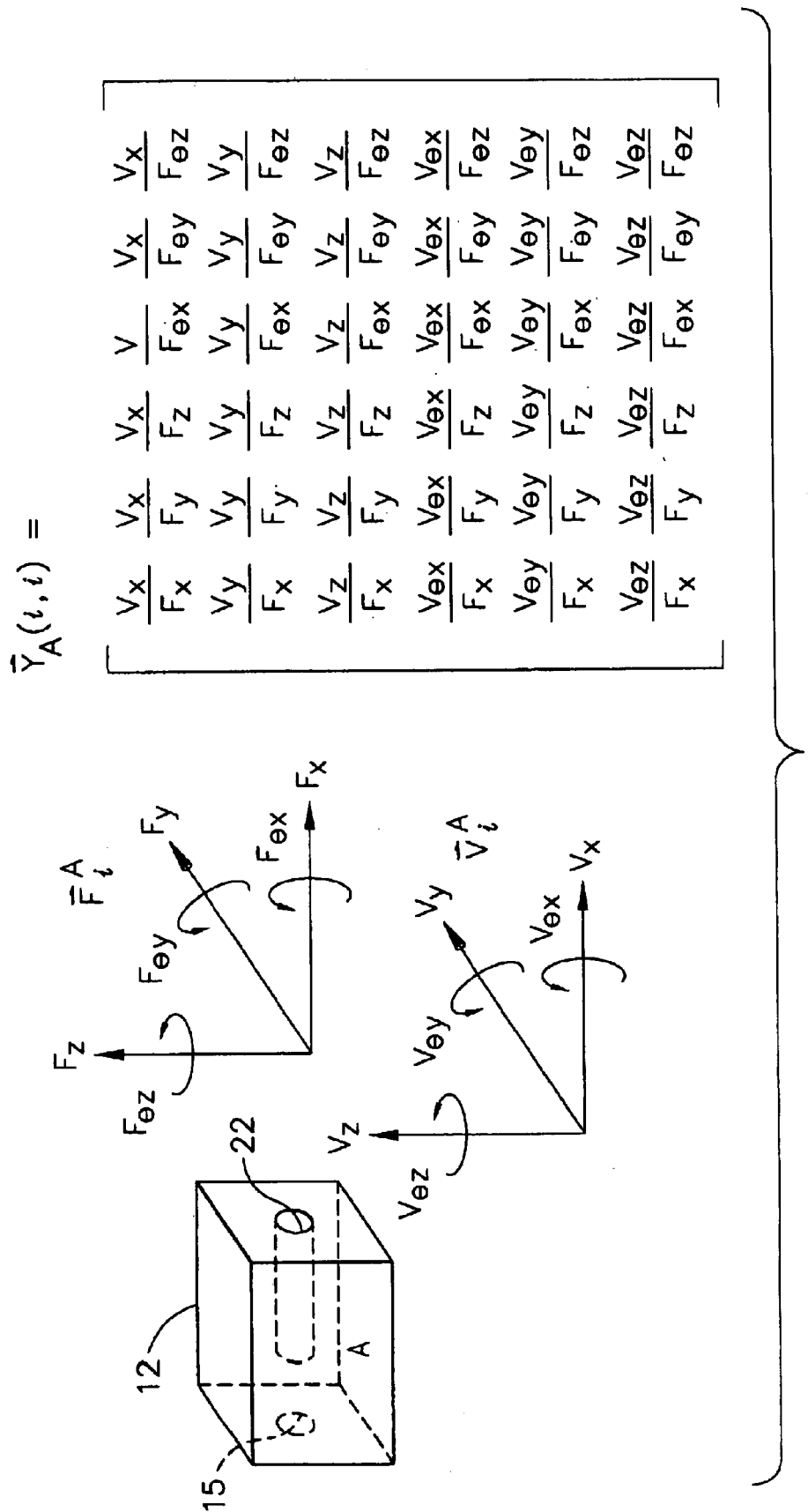
FIG. 3A shows a measured input subsystem interface transfer function when test relative forces are applied to the input subsystem shown in FIG. 2A according to the first embodiment of the methodology of the present invention.
Figure 3B:
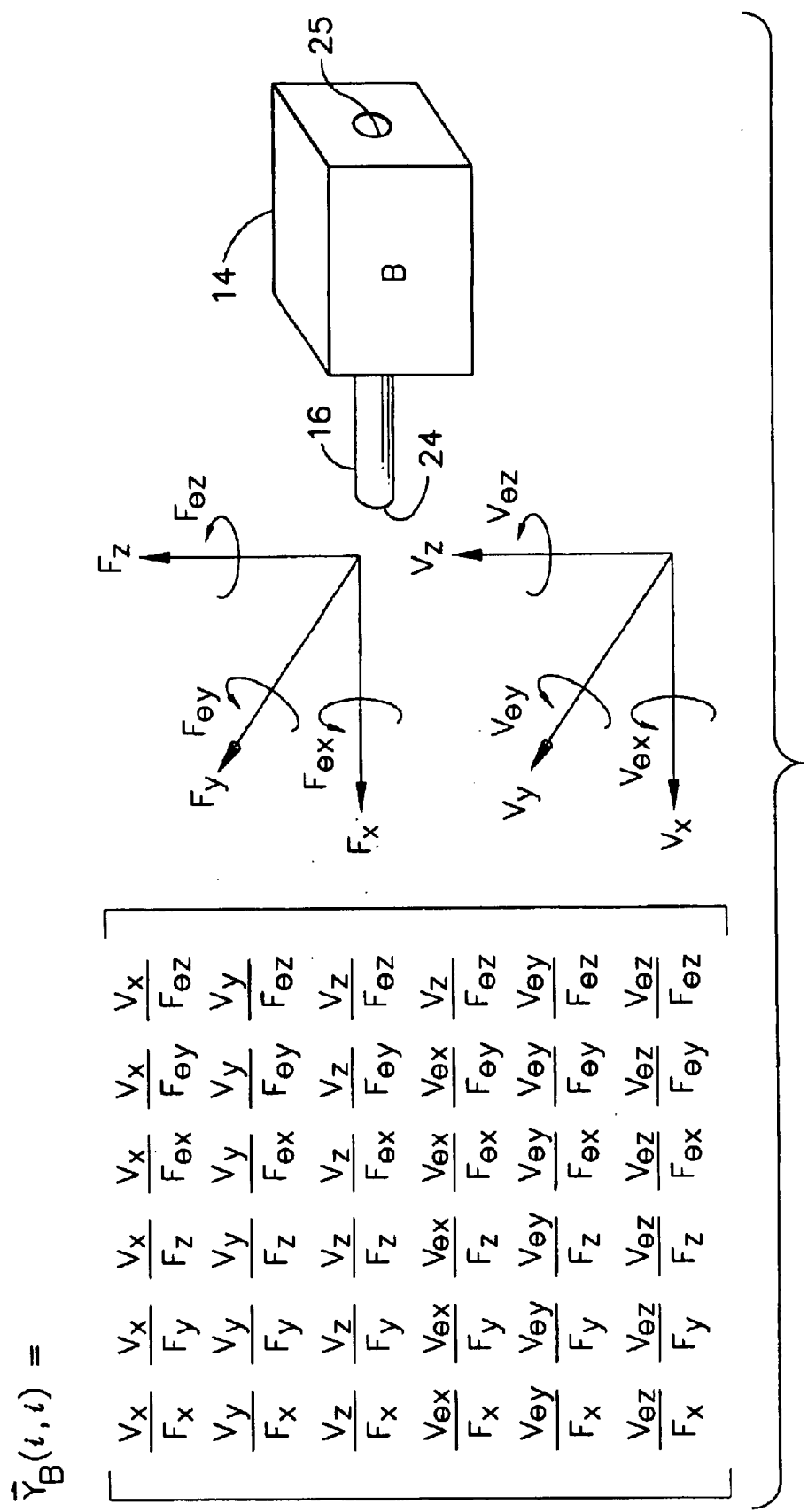
FIG. 3B shows an output subsystem interface transfer function when test relative forces are applied to the output subsystem shown in FIG. 2B according to the first embodiment of the methodology of the present invention.

Referring to FIGS. 3A–3B, a test relative force $F_i^A$ is applied to an interface point 22 of the input subsystem 12 and a test relative force $F_i^B$ is applied to an interface point 24 of the output subsystem 14. The test relative force is applied to the interface points 22, 24 at all interface degrees of freedom. More specifically, the test relative force is applied at all axes of direction in which the isolator 16 can communicate significant forces or torques. In the exemplary system 10 the isolator 16 can communicate forces and torques in the x, y and z directions. The test relative forces, in the present example, are applied as forces in the x, y and z directions ($F_x$, $F_y$, $F_z$) and also as a torque applied about the x, y and z axes ($F_{\theta x}$, $F_{\theta y}$, $F_{\theta z}$).

In a manner similar to the test input force, a sensor (such as sensor 19 shown in FIGS. 2A–2B) measures the motion of the input and output subsystems 12, 14 at the interface points 22, 24 in response to each of the test relative forces being applied to the interface points 22, 24. The interface point transfer functions of the input subsystem 12 and the output subsystem 14 are subsequently determined. The interface transfer function is a vector quantity that is related to the test relative forces by the following formulas:

$$Y_{a(i,i)} = \begin{vmatrix} V_x/F_x, V_x/F_y, V_x/F_z, V_x/F_{\theta x}, V_x/F_{\theta y}, V_x/F_{\theta z} \\ V_y/F_{xa}, V_y/F_y, V_y/F_z, V_y/F_{\theta x}, V_y/F_{\theta y}, V_y/F_{\theta z} \\ V_z/F_{xa}, V_z/F_y, V_z/F_z, V_z/F_{\theta x}, V_z/F_{\theta y}, V_z/F_{\theta z} \\ V_{\theta x}/F_{xa}, V_{\theta x}/F_y, V_{\theta x}/F_z, V_{\theta x}/F_{\theta x}, V_{\theta x}/F_{\theta y}, V_{\theta x}/F_{\theta z} \\ V_{\theta y}/F_{xa}, V_{\theta y}/F_y, V_{\theta y}/F_z, V_{\theta y}/F_{\theta x}, V_{\theta y}/F_{\theta y}, V_{\theta y}/F_{\theta z} \\ V_{\theta z}/F_{xa}, V_{\theta z}/F_y, V_{\theta z}/F_z, V_{\theta z}/F_{\theta x}, V_{\theta z}/F_{\theta y}, V_{\theta z}/F_{\theta z} \end{vmatrix} \quad (3)$$

for the input system 12; and $$Y_{b(i,i)} = \begin{vmatrix} V_x/F_x, V_x/F_y, V_x/F_z, V_x/F_{\theta x}, V_x/F_{\theta y}, V_x/F_{\theta z} \\ V_y/F_{xa}, V_y/F_y, V_y/F_z, V_y/F_{\theta x}, V_y/F_{\theta y}, V_y/F_{\theta z} \\ V_z/F_{xa}, V_z/F_y, V_z/F_z, V_z/F_{\theta x}, V_z/F_{\theta y}, V_z/F_{\theta z} \\ V_{\theta x}/F_{xa}, V_{\theta x}/F_y, V_{\theta x}/F_z, V_{\theta x}/F_{\theta x}, V_{\theta x}/F_{\theta y}, V_{\theta x}/F_{\theta z} \\ V_{\theta y}/F_{xa}, V_{\theta y}/F_y, V_{\theta y}/F_z, V_{\theta y}/F_{\theta x}, V_{\theta y}/F_{\theta y}, V_{\theta y}/F_{\theta z} \\ V_{\theta z}/F_{xa}, V_{\theta z}/F_y, V_{\theta z}/F_z, V_{\theta z}/F_{\theta x}, V_{\theta z}/F_{\theta y}, V_{\theta z}/F_{\theta z} \end{vmatrix} \quad (4)$$

for the output system 14.

Figure 4:
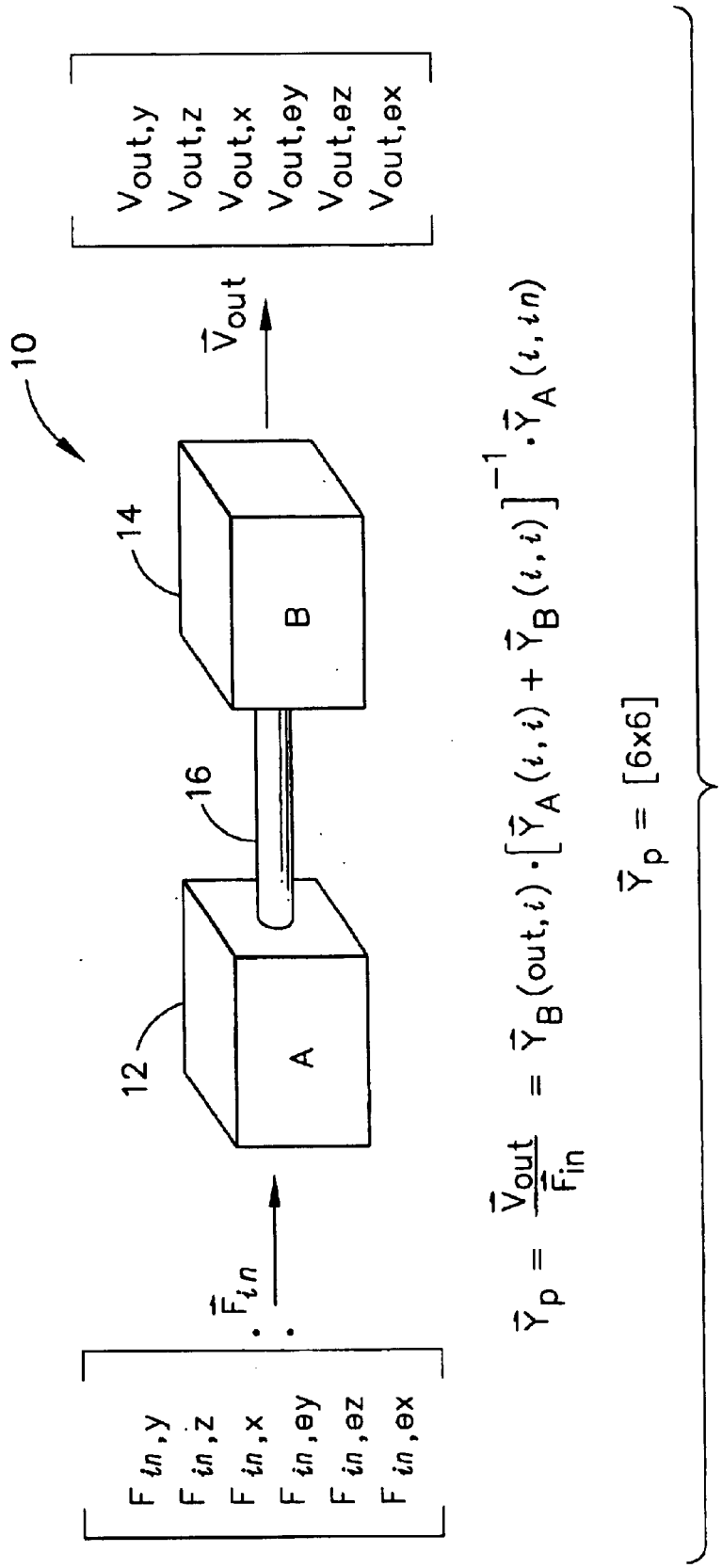
FIG. 4 shows a measured system performance function when a performance input force is applied to the exemplary system in FIG. 1 according to the first embodiment of the methodology of the present invention.

Referring to FIG. 4, a transfer function at a point of interest (performance output) of the system 10 is calculated. The performance function will determine the relative motion ($V_{out}$) of the output subsystem 14 in response to a disturbance force ($F_{in}$) being applied to the input subsystem 12 when both subsystems 12, 14 are coupled together via the isolator 16. Subsystems 12 and 14 are not connected before the performance function is calculated, as it is often economically unfeasible to measure the performance function of the system 10 in a manner similar to the transfer functions of the individual subsystems because the subsystems 12, 14 are frequently manufactured in different locations or are too large to couple together prior to the final assembly. In the present invention, the following formula is used to determine the performance function for the system 10:

$$V_{out} = Y_{b(out,i)} * [Y_{a(i,i)} + Y_{b(i,i)}]^{-1} * Y_{a(i,in)} * F_{in} \quad (5)$$

The performance function is calculated for each of the output performance degrees of freedom from each of the input disturbance degrees of freedom. The system 10 of FIG. 4 has performance functions for the x, y and z axes and rotation about the x, y and z axes. The performance function can subsequently be used by computer software to determine the dynamic effects on a point of interest of a subsystem as a result of a force being applied to another subsystem coupled to the subsystem having the point of interest.

Referring to FIGS. 5A–5D, a second embodiment of the methodology of the present invention will now be discussed. In the first embodiment, the isolator 16 and the output subsystem 14 are considered one subsystem for purposes of measuring the transfer functions. However, it may be economically unfeasible to connect the isolator 16 to the output subsystem 14 prior to measuring the transfer functions due to, for example, the isolator 16 and output system 14 being manufactured in different locations. Therefore, in the second embodiment of the present invention, the isolator 16 is defined as a separate subsystem.

The methodology for determining the transfer functions of the input subsystem 12 and the output subsystem 14 in the second embodiment is similar to that of the first embodiment. Referring to FIG. 5A, a test input force $F_{in}$ is applied to a drive point 15 of the input subsystem 12 while a sensor (such as sensor 19 shown in FIGS. 2A–2B) measures the motion $V_i^A$ at the drive point 15 to determine the drive point transfer function ($Y_A(i, in)$) of the input subsystem 12. A test relative force $F_i^A$ is applied to an interface point 22 of the input subsystem 12 at all degrees of freedom while a sensor measures the motion $V_i^A$ at the interface point at all degrees of freedom to determine the interface transfer function ($Y_A(i, i)$).

Referring to FIG. 5B, a test relative differential force ($F_i = F_i^B - F_i^A$) is applied at all degrees of freedom differentially between the ends of the isolator 16 where it couples with the input subsystem 12 and the output subsystem 14 while the sensor measures the differential motion to determine the isolator transfer function ($Y_i$). The isolator transfer function is related to the test relative differential force $F_i$ and the responding motion $V_i$ by the following formula:

$$Y_i = V_i/F_i; \text{ where } V_i = V_i^B - V_i^A. \quad (6)$$

Figure 5C:
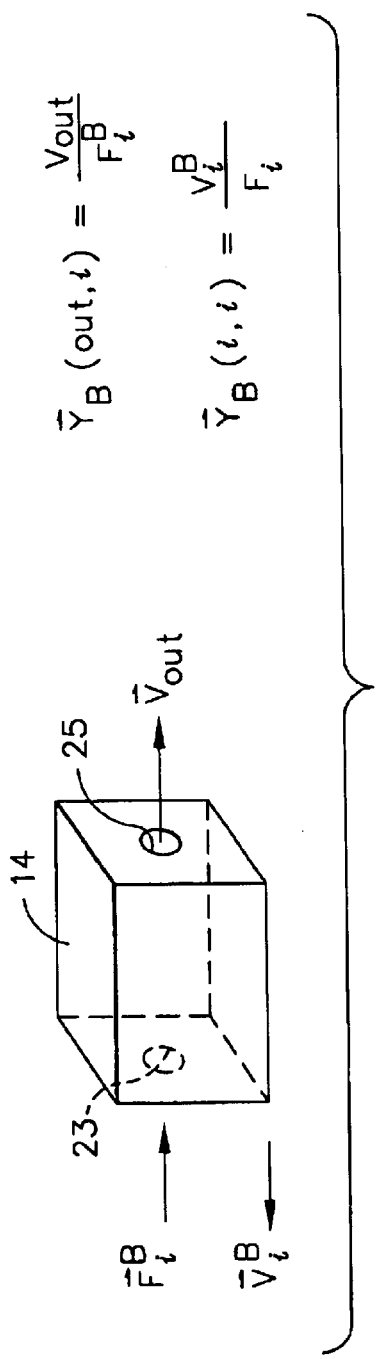

Referring to FIG. 5C, a test relative force $F_i^B$ is applied to an interface point 23 of the output subsystem 14 at all degrees of freedom while a sensor measures the motion $V_i^B$ at the interface point 23 at all degrees of freedom to determine the interface transfer function ($Y_B(i, i)$) and at the performance sensitive point 25 to determine the transfer function at the performance sensitive point ($Y_B(out, i)$).

Figure 5D:
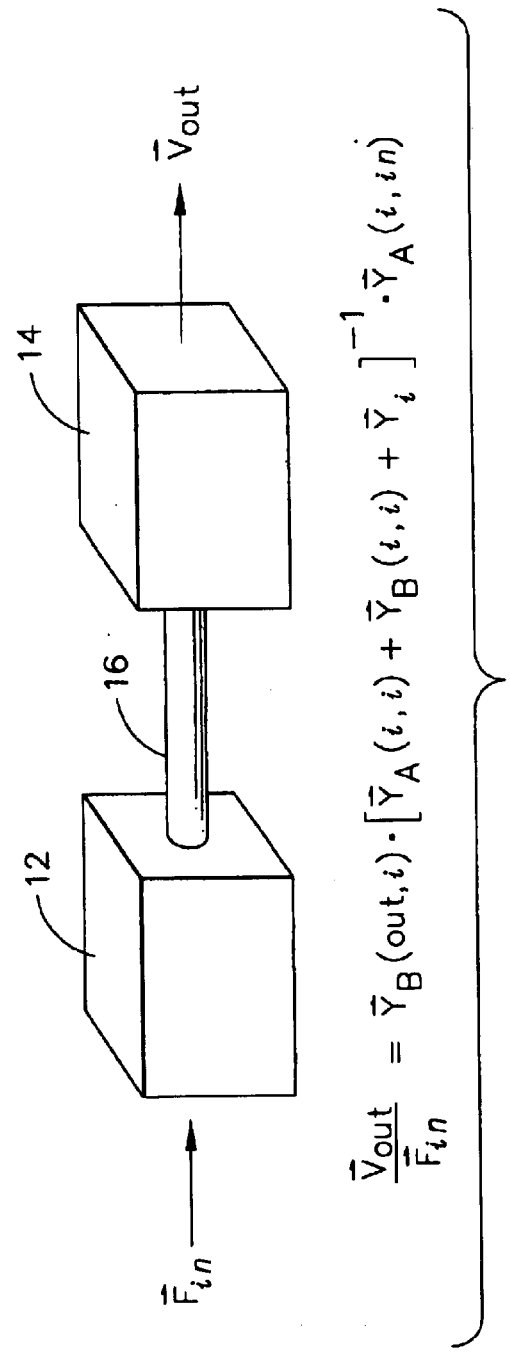

As shown in FIG. 5D, the performance function for the overall system 10 is determined by the following formula:

$$V_p = Y_B(out,i) * (Y_A(i,i) + Y_B(i,i) + Y_i)^{-1} * Y_A(i,in) * F_{in}. \quad (7)$$

The performance function is calculated for each of the degrees of freedom as in the first embodiment and is subsequently used to determine the dynamic effects ($V_{out}$) on a point of interest of a subsystem as a result of a disturbance $F_{in}$ being applied to another subsystem coupled to the subsystem having the point of interest.

Figure 6:
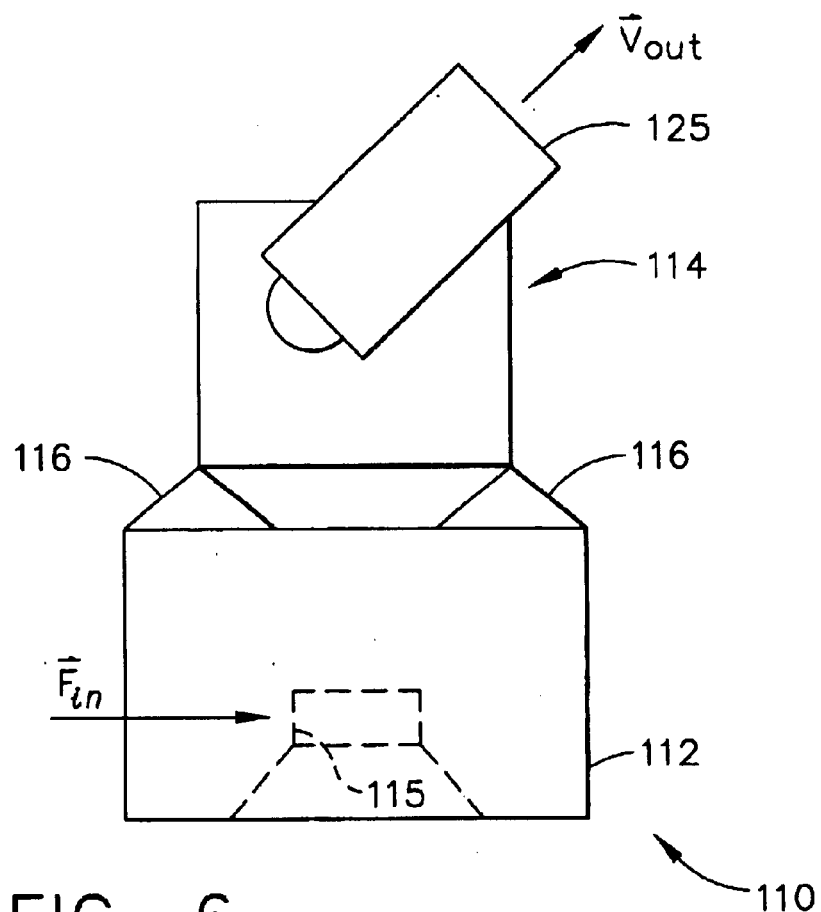
FIG. 6 shows a second exemplary system to be modeled and tested by the first embodiment of the methodology of the present invention.

Referring to FIG. 6, the methodology of the first embodiment of the present invention can be applied to a space system 110. In the system 110 a space bus 112 is coupled to a space payload 114 via an interface isolator 116. The space payload 114 can be, for example, a telescope, space vehicle, space camera, imaging system or any cargo that is sensitive to vibration. Vibration forces applied to the space bus 112 significantly affect the pointing angle of the space payload 114. Therefore, the performance function indicative of the relationship between the input forces and the movement of the space payload 114 must be determined. The performance function is determined in a similar manner to that of the first embodiment of the present invention.

Figure 7A:
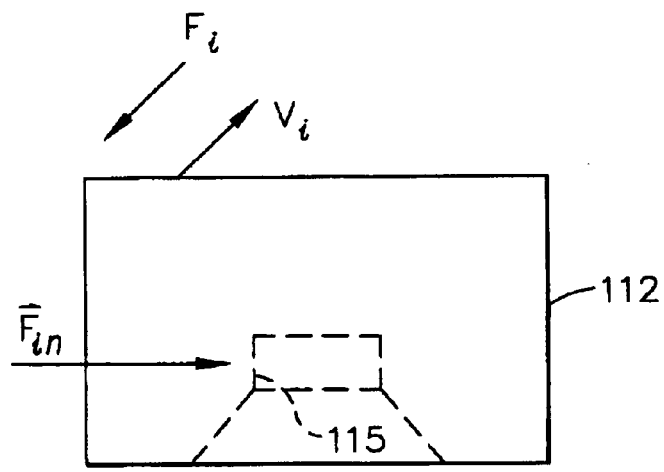
FIGS. 7A–7B show measured subsystem transfer functions for each subsystem of the second exemplary system in FIG. 6 according to the first embodiment of the methodology of the present invention.
Figure 7B:
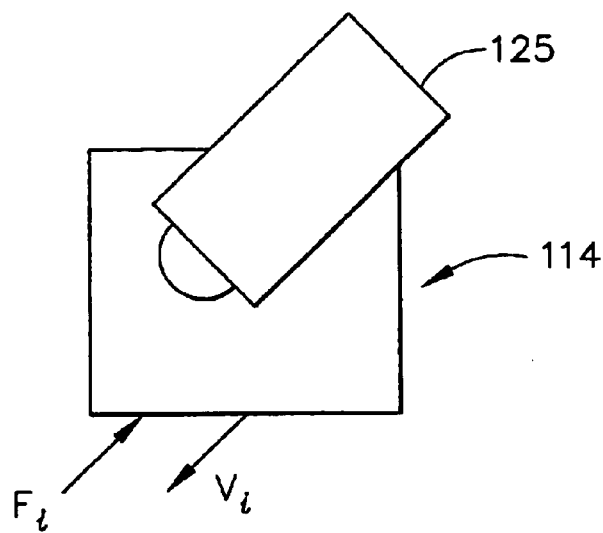

Referring to FIGS. 7A–7B, the space bus 112 and the space payload 114 are each separately tested to determine the transfer functions at the drive point 115 and the performance sensitive point 125. The interface transfer functions for the space bus 112 and the space payload 114 are then determined in a similar manner. The performance function for each of the output performance degrees of freedom can be calculated from the drive point and interface transfer functions.

The methodology of the present invention is not limited to the testing of two subsystems as shown in FIGS. 1–7. For example, referring to FIG. 8, the present invention can be applied to a system with numerous separately tested subsystems with numerous input forces. The system 10 includes a plurality of input subsystems 12a, 12b, 12c and an output subsystem 14, with each receiving a vibration force. Additional isolator elements (not shown), such as bolts, connect the plurality of input subsystems 12a, 12b, 12c to the output subsystem 14.

Figure 8:
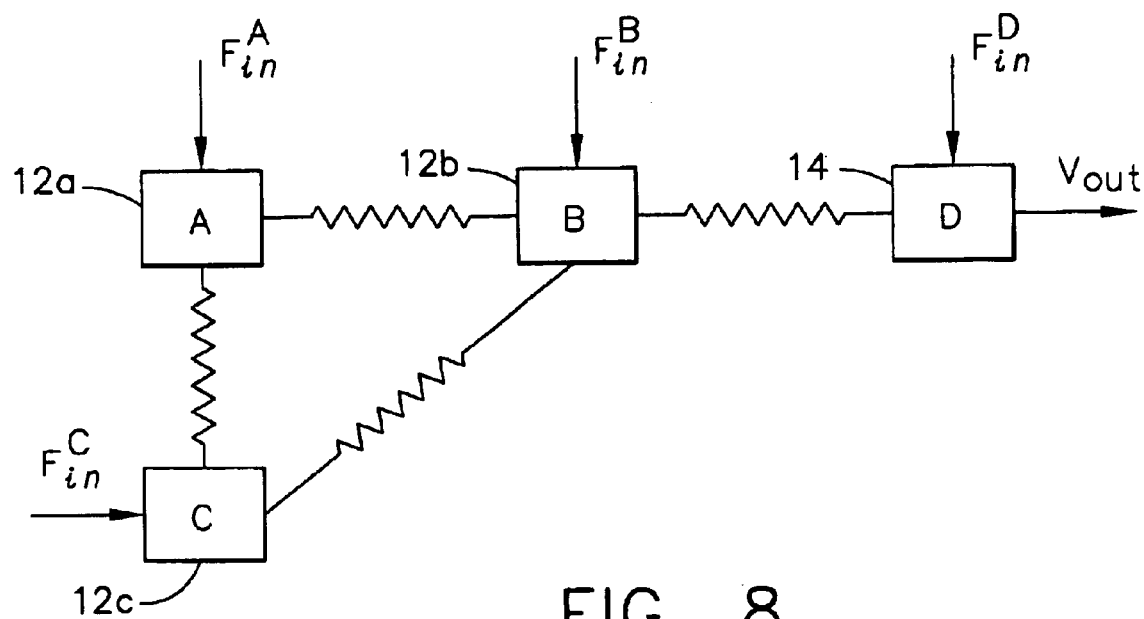
FIG. 8 shows a third exemplary system that can be tested by the methodology of the present invention.
Figure 9:
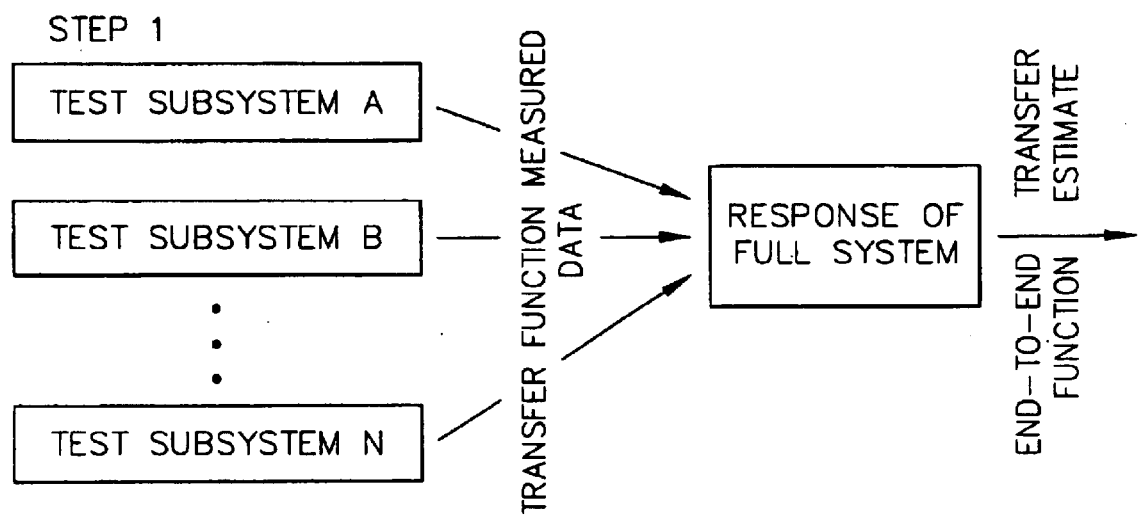
FIG. 9 is a flow diagram illustrating the methodology of the present invention when applied to a system with multiple input subsystems such as the system in FIG. 8.

The methodology for determining the performance function for the system of FIG. 8 is shown generally in the flow diagram in FIG. 9. The test input force and test relative force are applied to each individual subsystem, such as the subsystems 12a–12c, to measure the corresponding transfer functions for each subsystem. The performance function is determined in accordance with above-discussed Formula (7) by summing the drive point, the interface and the performance sensitive transfer functions respectively at their respective axes of degrees of freedom. The performance function can then be used to calculate the motion that will occur in the space payload 14 as a result of various forces being applied to the input subsystems 12a, 12b, 12c and the output subsystem 14.

While the above description is of the preferred embodiment of the present invention, it should be appreciated that the invention may be modified, altered, or varied without deviating from the scope and fair meaning of the following claims. For example, time domain or other excitation and sensing methods could be used rather than the transfer function measurements resulting from the above-discussed shaker or hammer excitation. Taking appropriate averages of the measurements using Fourier transforms could then create the transfer functions.

Figure 10:
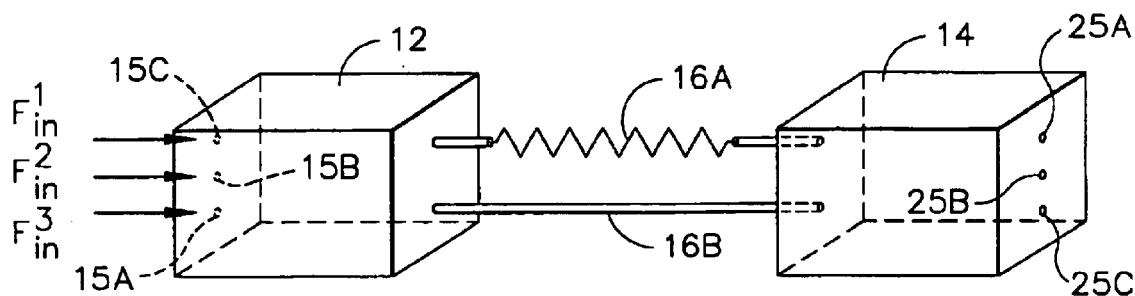
FIG. 10 shows a fourth exemplary system with numerous drive points, isolators and performance sensitive points that can be tested by the methodology of the present invention.

In the above examples, in determining the transfer functions for the input subsystems, only one input force was applied to one drive point and only one interface point was shown. However, it should be appreciated that the present invention is applicable even if, as shown in FIG. 10, the input subsystem has more than one drive point. In addition, the present invention is also applicable when there is more than one interface point between the subsystems and more than one performance sensitive point.

What is claimed is:

1. A method of estimating dynamics of a structural system, comprising:
    applying a test force to a subsystem;
    measuring one or more transfer functions for the subsystem from all respective interface degrees of freedom of interest in conjunction with the applying of the test force to the subsystem;
    determining one or more transfer functions of interest for the structural system subsequent to the measuring of the one or more transfer functions for the subsystem from all respective interface degrees of freedom of interest; and
    creating a system performance transfer function based on the determining of one or more transfer functions of interest.

2. The method of claim 1, wherein the measuring of one or more transfer functions for the subsystem from all respective interface degrees of freedom of interest in conjunction with the applying the test force to the subsystem comprises measuring a transfer function from all respective interface degrees of freedom between a drive point of a space bus and an interface point of the space bus.

3. The method of claim 1, wherein the measuring of one or more transfer functions for the subsystem from all respective interface degrees of freedom of interest in conjunction with applying the test force to the subsystem comprises measuring a transfer function from all respective interface degrees of freedom between an interface point of a space payload and a performance point of a space payload.

4. The method of claim 1, wherein the applying the test force to the subsystem comprises:
    applying a test input force to a drive point at a degree of freedom of an input subsystem;
    applying a test relative force to an interface point at a degree of freedom of the input subsystem at which the input subsystem interfaces with an output subsystem; and
    applying a test relative force to an interface point at the degree of freedom of the output subsystem at which the output subsystem interfaces with the input subsystem.

5. The method of claim 4, wherein the measuring of one or more transfer functions for the subsystem from all respective interface degrees of freedom of interest in conjunction with the applying the test force to the subsystem comprises:
    measuring a transfer function from the input force applied to the drive point of the input subsystem to the interface point of the input subsystem;
    measuring a transfer function from the test relative force applied to the interface point of the input subsystem to the interface point of the input subsystem;
    measuring a transfer function from the test relative force applied to the interface point of the output subsystem to a performance sensitive point of the output subsystem; and
    measuring a transfer function from the test relative force applied to the interface points of the output subsystem to the interface point of the output subsystem.

6. The method of claim 5, wherein the determining of one or more transfer functions of interest for the structural system subsequent to the measuring of the one or more transfer functions for the subsystem from all respective interface degrees of freedom of interest comprises:
    estimating a performance transfer function by applying a formula for all measured transfer functions of the input subsystem and the output subsystem, the formula being:

$$Y_p = (V_{out}/F_{in}) = Y_{b(out,i)} * [Y_{a(i,i)} + Y_{b(i,i)}]^{-1} * Y_{a(i,in)}$$

wherein $Y_p$ represents the performance transfer function, $Y_{b(out,i)}$ represents the transfer function measured from the test relative force applied to the interface point of the output subsystem to the performance sensitive point of the output subsystem, $Y_{a(i,i)}$ represents the transfer function measured from the test relative force applied to the interface point of the input subsystem to the interface point of the input subsystem, $Y_{b(i,i)}$ represents the transfer function measured from the test relative force applied to the interface point of the output subsystem to the interface point of the output subsystem, $Y_{a(i,in)}$ represents the transfer function measured from the test input force applied to the drive point of the input subsystem to the interface point of the input subsystem, $V_{out}$ represents a relative motion of system performance and $F_{in}$ represents a system drive point disturbance force.

7. The method of claim 4, wherein the applying the test input force to the drive point at the degree of freedom of the input subsystem, the applying the test relative force to the interface point at the degrees of freedom of the input subsystem and the applying the test relative force to the interface point at the degree of freedom of the output subsystem further comprises applying a vibrating force.

8. The method of claim 4, wherein the applying the test input force to the drive point at the degree of freedom of the input subsystem, the applying the test relative force to the interface point at the degrees of freedom of the input subsystem and the applying the test relative force to the interface point at the degree of freedom of the output subsystem further comprises applying a tapping force.

9. The method of claim 1, further comprising:
    applying a test input force to one or more drive points at degrees of freedom of each of a plurality of input subsystems that are all part of one system;

applying a test relative force to one or more interface points at degrees of freedom of each of the plurality of input subsystems and an output subsystem where each of the plurality of input subsystems and the output subsystem interfaces with another subsystem;

measuring a plurality of drive point transfer functions from the test input force applied to the one or more drive points of each of the plurality of input subsystems to the one or more interface points of each of the plurality of input subsystems;

measuring a plurality of interface transfer functions from the test relative force applied to the one or more interface points of each of the plurality of input subsystems and the output subsystem to the one or more interface points of each of the plurality of input subsystems and the output subsystem;

measuring a plurality of performance sensitive transfer functions from the test relative force applied to the one or more interface points of the output subsystem to one or more performance sensitive points on the output subsystem.

10. The method of claim 9, further comprising:

estimating a performance transfer function by applying a formula to the plurality of drive point, interface and performance sensitive transfer functions of each of the plurality of input subsystems and the output subsystem, the formula being:

$$Y_p = (V_{out}/F_{in}) = \Sigma Y_{b(out,i)} * [\Sigma Y_{a(i,i)} + \Sigma Y_{b(i,i)}]^{-1} * \Sigma Y_{a(i,in)}$$

wherein $Y_p$ represents the performance transfer function, $\Sigma Y_{b(out,i)}$ represents a sum of the plurality of performance sensitive transfer functions in a degree of freedom, $\Sigma Y_{a(i,i)}$ represents a sum of the plurality of interface transfer functions measured for each of the plurality of input subsystems in a degree of freedom, $\Sigma Y_{b(i,i)}$ represents a sum of the plurality of interface transfer functions measured for the output subsystem in a degree of freedom, $\Sigma Y_{a(i,in)}$ represents a sum of the plurality of drive point transfer functions measured for the plurality of input subsystems at a degree of freedom, $V_{out}$ represents a relative motion of system performance and Fh represents a system drive point disturbance force.

11. The method of claim 9, further comprising:

performing a Fourier analysis on a plurality of averages of the plurality of measured drive point transfer functions, interface transfer functions and performance sensitive functions to generate frequency domain descriptions of transfer functions of interest on the plurality of input subsystems and the output subsystem.

12. A method of analyzing data representative of transfer functions for each of a plurality of subsystems to determine a performance transfer function at a point of interest comprising:

determining a relative motion of system performance at the point of interest by applying a formula to all interface transfer functions at all interface degrees of freedom between each of the plurality of subsystems, to all drive point transfer functions at all drive point degrees of freedom of the plurality of subsystems and to each of all performance sensitive transfer functions at all performance sensitive degrees of freedom of the plurality of subsystems, the formula being:

$$Y_p = (V_{out}/F_{in}) = \Sigma Y_{b(out,i)} * [\Sigma Y_{a(i,i)} + Y_{b(i,i)}]^{-1} * \Sigma Y_{a(i,in)}$$

wherein $Y_p$ represents the performance transfer function at the point of interest, $\Sigma Y_{b(out,i)}$ represents a sum of the performance sensitive point of degrees of freedom of the output subsystem, $\Sigma Y_{a(i,i)}$ represents a sum of the interface transfer functions, $\Sigma Y_{a(i,in)}$ represents a sum of the drive point transfer functions, $V_{out}$ represents a relative motion of system performance and $F_{in}$ represents a system disturbance force.

13. A method of estimating dynamic performance of a payload that is in structural communication with a space bus comprising:

applying a test input force to each drive point of the space bus that is in direct structural communication with a corresponding isolator interface at an axis of structural communication;

applying a test relative force to each interface point of the space bus and to each interface point of the payload;

measuring transfer functions at all axes of structural communication in the apace bus and in the payload; and estimating a system dynamic payload transfer function at all axes of structural communication based upon the transfer functions measured at all axes of structural communication at the drive point of the space bus and at the payload.

14. The method of claim 13, wherein the measuring of the transfer functions at all axes of structural communication at the space bus and at the payload comprises:

measuring transfer functions of the payload $Y_{b(out,i)}$ at performance sensitive points of the payload as a result of force from the each interface point;

measuring transfer functions of the space bus $Y_{a(i,i)}$ at the each interface point as a result of force from the each interface point;

measuring transfer functions of the payload $Y_{b(i,i)}$ at the each interface point as a result of force from the each interface point; and measuring transfer functions of the space bus $Y_{a(i,in)}$ at the each interface point as a result of force from the each drive point of the space bus.

15. The method of claim 14, wherein the estimating of the system dynamic payload transfer function at all axes of structural communication based upon the transfer functions measured at all axes of structural communication in the space bus and in the payload comprises applying each of the plurality of transfer functions measured to a formula, the formula being:

$$V_{out} = Y_{b(out,i)} * [Y_{a(i,i)} + Y_{b(i,i)}]^{-1} * Y_{a(i,in)} * F_{in},$$

wherein $V_{out}$ represents the system dynamic payload performance sensitive motion and $F_{in}$ represents an input force applied to all axes of structural communication of each drive point of the plurality of subsystems.

16. The method of claim 13, wherein the applying of the test input force to the each drive point of the space bus further comprises applying the input force as a vibrating force at all axes of structural communication.

17. The method of claim 13, wherein the measuring of the transfer functions at all axes of structural communication in the space bus and in the payload comprises:

measuring transfer functions of the payload $Y_{B(i,i)}$ at each interface point of the payload as a result of force from the each interface points of the payload;

measuring transfer functions of the payload $Y_{B(out,i)}$ at performance sensitive points of the payload as a result of force from the interface points;

measuring transfer functions at ends of an interface isolator $Y_1$ that results from the relative force being applied to the ends of the interface isolator;

measuring transfer functions of an interface point of the space bus $Y_{A(i,i)}$ that results from force from the interface of the space bus; and measuring transfer functions from the each drive point of the space bus $Y_{A(i,in)}$ that results from the input force $F_{in}$.

18. The method of claim 17, wherein the estimating of the system dynamic payload transfer function at all of structural communication functions measured comprises applying the transfer functions measured to a formula, the formula being:

$$V_{OUT} = Y_{B(out,i)} * [Y_{A(i,i)} + Y_{B(i,i)} + Y_1]^{-1} * Y_{A(i,in)} * F_{in},$$

wherein $V_{OUT}$ represents the payload performance sensitive point and $F_{in}$ represents the drive force applied to the each drive point of the space bus.

19. The method of claim 13, wherein the applying of the test input force to the each drive point of the space bus comprises vibrating the space bus at a disturbance entry point.

20. The method of claim 13, wherein the applying of the test input force to the each drive point of the space bus comprises tapping the space bus at a disturbance entry point.

21. The method of claim 13, wherein the applying of the test input force to the each drive point of the space bus comprises tapping the space bus at a disturbance entry point where the space bus includes a disturbance source consisting of rotating or oscillating equipment.

22. The method of claim 13, wherein the measuring of the transfer functions of the payload comprises measuring the transfer function of an item selected from the group consisting of: space telescope, apace vehicle, space camera, imaging system and communication antenna.

23. A method of determining a performance function of a space structural system comprising:

applying a test input force to a drive point of a plurality of subsystems;

applying a test relative force to at least one interface point of each of the plurality of input subsystems where each of the plurality of input subsystems interfaces with at least another one of the plurality of subsystems;

measuring a drive point transfer function for each of the plurality of subsystems that is a result of the applying of the test input force;

measuring an interface transfer function for each of the plurality of subsystems that is a result of the applying of the test relative force;

measuring a performance sensitive transfer function that is a result of the applying of the test relative force to one of the plurality of subsystems;

creating a transfer function of performance based on the measured drive point transfer functions, interface transfer functions and the performance sensitive transfer function.

* * * * *